United States Patent
Brody (10) Patent No.: US 11,065,418 B1
(45) Date of Patent: Jul. 20, 2021

(54) BLADDER STORAGE ANOMALY ASSESSMENT

(71) Applicant: SRS Medical Systems, LLC, North Billerica, MA (US)

(72) Inventor: Lee Brody, Somerville, MA (US)

(73) Assignee: SRS Medical Systems, LLC, North Billerica, MA (US)

(*) Notice: Subject to any disclaimer, the term of this patent is extended or adjusted under 35 U.S.C. 154(b) by 130 days.

(21) Appl. No.: 16/551,807

(22) Filed: Aug. 27, 2019

Related U.S. Application Data (63) Continuation-in-part of application No. 15/695,249, filed on Sep. 5, 2017, now Pat. No. 10,485,483.

(Continued)

(51) Int. Cl.
    *A61B 5/00* (2006.01)
    *A61M 25/10* (2013.01)
    (Continued)

(52) U.S. Cl.
    CPC ......... *A61M 25/0017* (2013.01); *A61B 5/205* (2013.01); *A61M 25/04* (2013.01);
    (Continued)

(58) Field of Classification Search
    CPC ... A61B 5/6853; A61B 5/036; A61B 5/04012; A61B 5/0488; A61M 25/10185; A61M 25/0017
    (Continued)

(56) References Cited

U.S. PATENT DOCUMENTS 5,100,394 A * 3/1992 Dudar ................... A61J 1/2089
                                                              604/537
5,314,411 A   5/1994 Bierman et al.
(Continued)

FOREIGN PATENT DOCUMENTS

CN    104856665 A    8/2015
GB      2395128 A    5/2004

OTHER PUBLICATIONS

Extended European Search Report from EP17861666.0; 16 pages; Philippe Rolland; dated May 19, 2020.
(Continued)

*Primary Examiner* — Erin M Piateski
(74) *Attorney, Agent, or Firm* — Dicke, Billig & Czaja, PLLC (57) ABSTRACT

A method of assessing bladder storage anomalies via utilization of an indwelling urinary drainage catheter is provided. A urodynamic assessment assembly is provided, the assembly characterized by a pressure sensor for vesical pressure measurement, a processor/controller for receiving, processing and/or displaying select urodynamic patient parameters comprising sensed/monitored pressure data, and a catheter balloon adaptor for operably uniting the pressure sensor of the urodynamic assessment assembly to a balloon inflation valve of the indwelling urinary drainage catheter, the indwelling urinary drainage catheter operably linked with the urodynamic assessment assembly. Vesical pressure is sensed via the vesical pressure sensor during a bladder emptying event, the bladder emptying event characterized by an application of variable resistance to fluid flow from the bladder via the indwelling urinary drainage catheter with vesical pressure/outlet resistance/flow rate relationships established based upon sensed vesical pressure values.

10 Claims, 8 Drawing Sheets

Related U.S. Application Data (60) Provisional application No. 62/510,795, filed on May 25, 2017, provisional application No. 62/467,520, filed on Mar. 6, 2017, provisional application No. 62/408,908, filed on Oct. 17, 2016, provisional application No. 62/724,885, filed on Aug. 30, 2018.

(51) Int. Cl.
| | | |
|---|---|---|
| *A61B 5/04* | (2006.01) | |
| *A61B 5/03* | (2006.01) | |
| *A61M 25/00* | (2006.01) | |
| *A61B 5/0488* | (2006.01) | |
| *A61M 25/04* | (2006.01) | |
| *A61B 5/20* | (2006.01) | |
| *A61M 27/00* | (2006.01) | |

(52) U.S. Cl.
CPC ............ *A61B 5/204* (2013.01); *A61M 25/10* (2013.01); *A61M 27/008* (2013.01); *A61M 2025/0001* (2013.01); *A61M 2210/1085* (2013.01)

(58) Field of Classification Search
USPC ........................................................ 600/301
See application file for complete search history.

(56) References Cited

U.S. PATENT DOCUMENTS

| | | | |
|---|---|---|---|
| 5,573,007 A | 11/1996 | Bobo, Sr. | |
| 5,617,876 A | 4/1997 | Van Duyl | |
| 5,916,153 A | 6/1999 | Rhea, Jr. | |
| 5,951,497 A | 9/1999 | Wallace et al. | |
| 5,984,879 A | 11/1999 | Wallace et al. | |
| 6,021,781 A | 2/2000 | Thompson et al. | |
| 6,434,418 B1 | 8/2002 | Neal et al. | |
| 6,447,462 B1 * | 9/2002 | Wallace | A61B 5/202 600/435 |
| 7,004,899 B2 | 2/2006 | Tracey | |
| 7,766,870 B2 | 8/2010 | Dabbs | |
| 8,192,368 B2 | 6/2012 | Woodruff et al. | |
| 8,337,411 B2 | 12/2012 | Nishtala et al. | |
| 8,535,237 B2 | 9/2013 | Nishtala | |
| 2004/0176703 A1 | 9/2004 | Christensen et al. | |
| 2006/0271019 A1 * | 11/2006 | Stoller | A61M 27/002 604/544 |
| 2006/0276712 A1 | 12/2006 | Stothers et al. | |
| 2007/0010761 A1 | 1/2007 | Mo | |
| 2009/0221933 A1 * | 9/2009 | Nishtala | A61B 5/205 600/561 |
| 2012/0041334 A1 | 2/2012 | Goedje et al. | |
| 2012/0046649 A1 | 2/2012 | Bierman | |
| 2013/0267868 A1 | 10/2013 | Connors et al. | |
| 2014/0275839 A1 * | 9/2014 | Kron | A61B 5/6834 600/301 |
| 2016/0183819 A1 * | 6/2016 | Burnett | A61B 5/14507 600/309 |
| 2016/0310077 A1 * | 10/2016 | Hunter | A61B 5/00 |
| 2016/0310711 A1 * | 10/2016 | Luxon | A61M 1/0031 |

OTHER PUBLICATIONS

International Search Report and Written Opinion from PCT/US2017/056905; 9 pages; Lee W. Young; dated Jan. 8, 2018.
International Preliminary Report on Patentability (IPRP) from PCT/US2017/056905; 7 pages; Lee W. Young; dated Apr. 23, 2019.
Chinese Office Action for appln. No. 201780063931.8, dated Mar. 18, 2021, 55 pages with machine translation.

* cited by examiner

BLADDER STORAGE ANOMALY ASSESSMENT

This is a United States continuation-in-part patent application filed pursuant to 35 USC § 111(a) and 37 CFR § 1.53(b) claiming priority under 35 USC § 120 of/to U.S. patent application Ser. No. 15/695,249 filed Sep. 5, 2017, entitled DIAGNOSTIC DRAINAGE CATHETER ASSEMBLY & METHODS, said application claiming priority under 35 USC § 120 of/to U.S. Pat. Appl. Ser. No. 62/510,795 filed May 25, 2017, U.S. Pat. Appl. Ser. No. 62/467,520 filed Mar. 6, 2017, and U.S. Pat. Appl. Ser. No. 62/408,908 filed Oct. 17, 2016, each entitled DIAGNOSTIC DRAINAGE CATHETER ASSEMBLY, and U.S. Pat. Appl. Ser. No. 62/724,885 filed Aug. 30, 2018, entitled DIAGNOSTIC DRAINAGE CATHETER ASSEMBLY; MEASUREMENT OF BLADDER VESICAL PRESSURE USING A DRAINAGE CATHETER the disclosures of which are hereby incorporated by reference in their entireties.

TECHNICAL FIELD

The present invention is generally directed to bladder storage anomaly assessment, more particularly but not exclusively, to improved cystometric test methodologies and assemblies for conducting same, for the sake of, among other things, patient self-void ability determination in furtherance of a desire to have an indwelling urinary drainage catheter deployed for no longer than is necessary.

BACKGROUND

A urinary catheter is a hollow, partially flexible tube that permits the free passage or drainage of urine from the bladder for external collection via a drainage bag or the like. The catheter is inserted into an individual's bladder via the urethra, effectively short circuiting the anatomy/physiology of the lower urinary tract (i.e., creates a low resistance channel to passively drain the bladder, often to an external urine collection device). The catheter may be one that stays in place throughout the day (i.e., an indwelling urinary catheter commonly characterized by a bladder anchor structure, e.g., an inflatable balloon), or an intermittent catheter which is inserted and removed each time the bladder is drained.

Catheters are utilized for several different clinical reasons such as urinary incontinence (i.e., leaking urine or being unable to control when you urinate), or following lower urinary tract surgery in which the surgeon is looking to avoid filling the bladder and/or having the urine come in contact with the urethra immediately following a medical procedure. More usually, a urinary catheter is utilized when a patient has symptoms of urinary retention (i.e., being unable to empty your bladder when you need to), a medical condition, or surgery. Excessive urine accumulation in the bladder may cause pain, bladder injury and/or reflux of urine through the ureters into the kidneys.

Most catheters are a short term fix (i.e., temporary), necessary only until the ability to self-void can be reliably and safely demonstrated, however, circumstances abound which warrant a lengthy deployment (i.e., chronic).

Each year in the United States, more than a million patients receive an indwelling urinary catheter due to urinary retention. Urinary retention often occurs when the bladder vesical pressure does not adequately overcome the bladder outlet resistance, resulting in an inability to adequately empty the bladder. These episodes are often temporary and the drainage catheter can eventually be removed. Many of these retention events occur in hospitals as a result of temporary impairment of vesical pressure.

Hospitals and urology practices have difficulty predicting when an individual no longer needs a urinary catheter to empty his or her bladder. The use of urinary catheters comes with a high incidence of medical complications, including urinary tract infections, known as catheter associated urinary tract infections (CAUTIs), the most common type of healthcare associated infection. Traditionally, caregivers may have erred on the side of leaving the catheter in too long, resulting in high rates of CAUTIs.

The Centers for Disease Control and Prevention (CDC) estimates 13,000 U.S. patient deaths each year due to CAUTIs, an excess length of stay of two to four days, an unnecessary antimicrobial use, and an increased cost of $0.4-0.5 billion nationally per year ("Catheter-associated Urinary Tract Infection (CAUTI) Toolkit," Carolyn Gould, MD MSCR). Due to an increased awareness of catheter-related medical complications and various emerging healthcare economic incentives, including financial penalties directly tied to rates of CAUTIs, the protocols for the removal of urinary catheters have become more aggressive and have resulted in increased incidents of bladder injury due to retention events after premature removal of the urinary catheter.

There are a wide range of clinical protocols to determine whether a catheter can be removed, often dependent on place-of-service and whether a urologist is involved in the protocol. These varying protocols commonly involve the removal of the catheter without an assessment of vesical pressure; the bladder is simply allowed to fill, either naturally or artificially, and observations over time as to whether the patient remains in urinary retention are made, with a bladder ultrasound oftentimes used to measure post void residual urine remaining in the bladder. If the patient cannot adequately void, a catheter is again placed in the bladder. This is an expensive protocol, requiring highly organized and lengthy clinical supervision to determine whether the catheter needs to be replaced. Complications of this protocol include inadvertent overfilling of the bladder during retention events (i.e., bladder distention) as well as the known increase in CAUTI risk owing to the process of reinserting a catheter that was prematurely removed.

As was previously referenced, bladder vesical pressure determinations and assessment are important indicators of lower urinary tract functionality, and a critical component of a urodynamic study. The measurement of bladder vesical pressure using a standard indwelling (Foley) drainage catheter deployed for that purpose is currently a gold standard for the diagnosis of intra-abdominal hypertension (IAH) and abdominal compartment syndrome (ACS). Historically, Foley catheters have been specifically deployed and utilized to measure vesical pressure as part of a urodynamics examination for various assessments of bladder dysfunction.

The Foley catheter, named for its designer Boston surgeon Frederic Foley, is by far the most common type of indwelling urinary catheter. For all intents and purposes, the Foley catheter is the standard-of-care device to address retention.

Figure 1A:
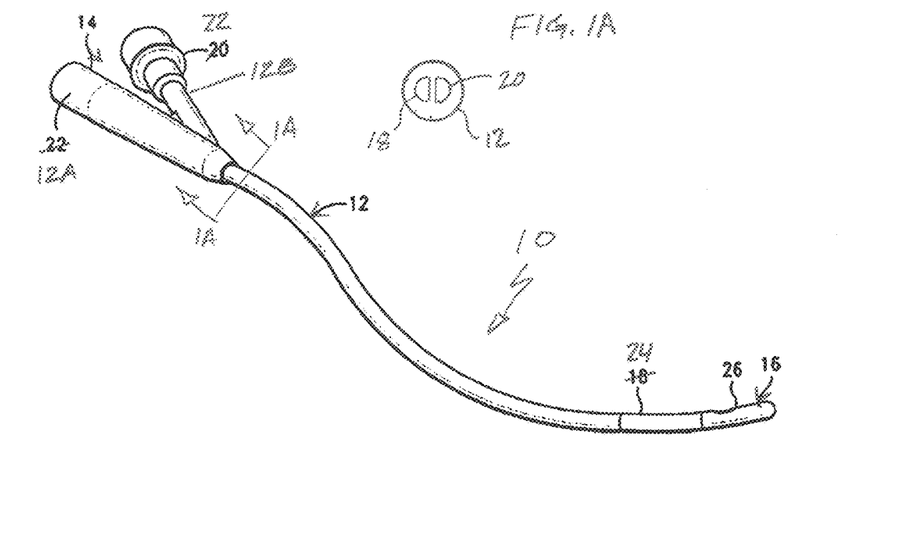
FIG. 1A is a section of the catheter of FIG. 1, more particularly, a section about line 1A thereof.

With reference to FIG. 1, Foley catheter 10 generally comprises a body 12 (e.g., tube) characterized by proximal 14 and distal 16 end portions, and two discrete channels or lumens, namely, a drain lumen 18, and an inflation lumen 20 (FIG. 1A).

Proximal portion 14 of tube 12 is characterized by a bifurcation which delimits a drain segment 12A, characterized by lumen 18, and an inflation segment 12B, characterized by lumen 20. Drain segment 12A is adapted for operative union with a urine collection system, commonly a urine collection device and a valve for regulating urine discharge/collection. Inflation segment 12B is adapted to include an inflation valve 22.

Distal portion 16 of tube 12, the insertion end, includes an anchoring structure in the form of an inflatable balloon 24. Balloon 24 is operatively linked to inflation valve 22 via lumen 20 in furtherance of select inflation (i.e., expansion) of the inflatable balloon, commonly with sterile water, once distal end portion 14 is suitably positioned in the bladder. Moreover, distal portion 16 of tube 14 includes a urine ingress port in the form of an aperture 26 in a sidewall of tube 12, with drain lumen 18 terminating at or combining with the aperture so as to delimit and function as a urine conduit, draining urine from the bladder to and into the external collection bag.

In bladder pressure related assessment applications, a standard 2-way or 3-way Foley catheter is placed into the bladder, the former characterized by one balloon fill port and one urine drainage port, the latter by one balloon fill port and two urine drainage ports. Fluid, commonly sterile water, is introduced into the anchoring balloon to enable retention of the device via cooperative engagement of the fluid filled balloon with the bladder outlet/bladder neck.

Depending on the clinical application, the bladder may be artificially filled with fluid, often sterile water, through the drainage line of the catheter. A pressure transducer is connected to the urine drainage line to indicate/measure the vesical pressure. The pressure transducer may be designed to prevent urine from draining through the urine drainage line, thus, a 3-way catheter is often chosen for continuous monitoring as drainage can continue to occur through the primary drainage line.

In the application of the diagnosis of IAH or ACS, continuous monitoring of the vesical pressure provides insight into the state of the intra-abdominal pressure. Typical clinical applications include emergency trauma and acute care surgery patients who are at risk of IAH and resultant organ dysfunction. In the application of assessment of bladder dysfunction, the vesical pressure is often monitored while the bladder is being filled and when the bladder is emptying through the catheter.

Numerous specialty catheters (i.e., functionally specific devices, with form fitting function) are known and available to support urodynamic assessments (see e.g., Rhea, Jr. (U.S. Pat. No. 5,916,153), Neal et al. (U.S. Pat. No. 6,434,418), Wallace et al. (U.S. Pat. No. 6,447,462), Tracy (U.S. Pat. No. 7,004,899), Woodruff et al. (U.S. Pat. No. 8,192,368), and Burnett et al. (US 2016/0183819). Each disclosed device of these exemplary teachings are intended to replacement or supplement the standard urinary drainage catheter. In-as-much as specialty catheters have been well received, there is a general and continuing appreciation to leverage the fact that individuals present for bladder storage anomaly assessment in a catheterized condition. In this vein, devices/systems (i.e., hardware—pieces and parts) for sensing bladder pressure and/or other urodynamic parameters, predicated upon use of indwelling drainage catheter, are known and commercially available (see e.g., Goedje et al. (US 2012/0041334), and the work of Nishtala (U.S. Pat. Nos. 8,337,411 & 8,535,237).

While enhanced techniques and improved approaches to bladder storage anomaly assessment, including provisions for novel assemblies or devices to support such assessments, are inherently advantageous, a less is more approach is especially advantageous and desirable per se, and in relation to prediction and/or determination of whether an individual can void without use of the indwelling urinary catheter. A coarse versus granular approach is believed desirable, with a critical unmet need remaining in relation to low risk high reward patient care pathway determination relative to improved patient outcomes. Thus, the subject disclosure is directed to bladder storage anomaly assessment generally, and assessment/determination of an individual's ability to self-void part-and-parcel of an advantageous, right fit care pathway determination characterized by minimal catheterization times.

SUMMARY OF THE INVENTION

A method of assessing bladder storage anomalies via utilization of an indwelling urinary drainage catheter is provided. A urodynamic assessment assembly is notionally and generally provided, the assembly characterized by a pressure sensor for vesical pressure measurement, a processor/controller for receiving, processing and/or displaying select urodynamic patient parameters comprising sensed/monitored pressure data, and an adaptor or fixture for operably uniting the pressure sensor of the urodynamic assessment assembly to a balloon inflation valve of the indwelling urinary drainage catheter, the indwelling urinary drainage catheter operably linked with the urodynamic assessment assembly. Vesical pressure is sensed via the vesical pressure sensor during a bladder emptying event, the bladder emptying event characterized by an application of variable resistance to fluid flow from the bladder via the indwelling urinary drainage catheter with vesical pressure/outlet resistance/flow rate relationships established based upon sensed vesical pressure values.

The application of variable resistance to fluid flow from the bladder, via the indwelling urinary drainage catheter, effectuated by mechanical means such as a fluid flow regulator associated with the drainage catheter, results in a pulsed fluid flow from the indwelling urinary drainage catheter. The resulting pulsed flow may be a regularly pulsed fluid flow, or an irregularly pulsed fluid flow. Moreover, and advantageously, applied variable resistance takes the form of alternating between a first applied resistance and a second applied resistance, the first applied resistance corresponding to a no fluid condition from the indwelling urinary catheter, the second applied resistance of applied variable resistance corresponds to a maximum flow condition from the indwelling urinary drainage catheter.

Further contemplated non-limiting method steps include, but are not limited to, each of the following, alone or in select combination: determining a fluid flow rate for fluid flowing from the bladder via the indwelling urinary drainage catheter during the bladder emptying event; determining a mass of fluid flowing from the bladder via the indwelling urinary drainage catheter during the bladder emptying event as a function of time; and/or, sensing vesical pressure via the vesical pressure sensor during a bladder fill event characterized by a no drainage condition/configuration for the indwelling urinary drainage catheter. In the case of the bladder fill event comprising a gravity fluid feed, a preferred approach further contemplates determining gravity fluid feed rates associated with the gravity fluid feed corresponding to select sensed vesical pressures while fluid fills and accumulates in the bladder. More specific features and advantages obtained in view of the summarized features will become apparent with reference to the drawing figures and DETAILED DESCRIPTION OF THE INVENTION.

BRIEF DESCRIPTION OF THE DRAWINGS

All figures have been prepared, and are included to facilitate and/or enhance an understanding of the basic teachings of the contemplated embodiments, and/or the concepts underlying same and are incorporated in and constitute a part of this specification. While the drawings illustrate embodiments and context with respect thereto, and together with the description serve to explain principles of embodiments, other embodiments and many of the intended advantages of the disclosed systems, subsystems, assemblies, subassemblies, apparatus, device, mechanism, etc. will be readily appreciated as they become better understood by reference to the following detailed description and figures. It is to be noted that the elements of the drawings are not necessarily to scale relative to each other, with like reference numerals designating corresponding similar parts/structures.

FIGS. 1-10 are provided herewith wherein:

FIG. 1 depicts an indwelling urinary drainage catheter, namely, a Foley catheter;

FIG. 8 depicts, perspective overhead view from the right, a first housing portion of a housing of the assembly of the combination of FIG. 6;

DETAILED DESCRIPTION OF THE INVENTION

Figure 2:
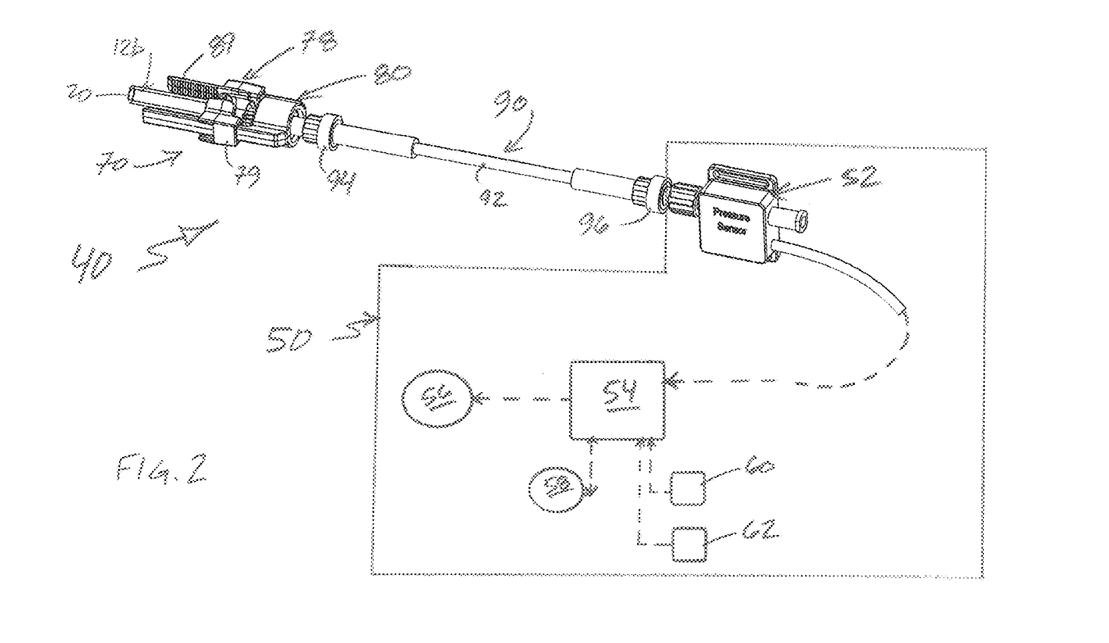
FIG. 2 depicts preferred, non-limiting components, in operative combination, of an advantageous diagnostic drainage catheter system for use with the catheter of FIG. 1.

Preferred, non-limiting systems, kits, assemblies, structures and/or mechanisms relating to and enabling assessment of patient urodynamics are generally disclosed, presented and/or represented throughout the figures of the subject disclosure. An advantageous, non-limiting system is generally depicted in FIG. 2 for operative combination with the indwelling urinary catheter of FIG. 1. Several advantageous, non-limiting adaptor assemblies of the contemplated system are generally depicted in each of FIGS. 3, 5 & 6, with FIGS. 7-9 directed to particulars for/of select depicted assemblies. Finally, representative urodynamic test parameters are shown (FIG. 11) in furtherance of disclosure and discussion of improved bladder storage anomaly assessment, and a desire for "right time" removal of an indwelling urinary drainage catheter.

Advantageously, Applicant's diagnostic approach is directed to individuals (i.e., patients) that have been catheterized and are, at the time of assessment, subject of indwelling urinary catheterization. A lesser/least invasive approach is welcome and valued by all stakeholders.

Moreover, a less-is-more system or kit approach is contemplated, with a system or kit that lacks the heretofore known complexity and that is especially user friendly is likewise viewed as welcome and valued by all stakeholders. Further still, in-as-much as the scope of contemplated diagnostics may be robust/varied, an important overarching objective of the contemplated diagnostic system or kit is an informed, get-it-right-the-first-time removal of the indwelling device from the patient. Predictive protocols with regard to catheter removal are enabled and hereinafter disclosed via vesical pressure measurement and assessment while the indwelling catheter is in place, with such approach welcome and valued by all stakeholders.

Finally, an easy to use, secure linkage assembly is provided for operatively uniting the indwelling urinary catheter, via its balloon inflation valve, to/with a pressure sensing element. Notionally, a "clamp" is provided which effectively deactivates the catheter's luer-actuated value, part-and-parcel of the balloon fill line thereof, via a clamp valve of the clamp, the clamp being lockable relative to the catheter/catheter luer-actuated balloon inflation valve. Moreover, an optional valved extension assembly is provided, a first valve thereof effectively disabling the clamp valve, the second, downstream valve for operative union with a urodynamic data system input/inflow (e.g., pressure sensor). Further still, the contemplated urodynamic data system input/inflow, advantageously, but not exclusively characterized by a pressure transducer, connects to a linkage assembly valve, e.g., the clamp valve or the second valve of the valved extension assembly, so as to deactivate same, the pressure from the balloon fill line thusly directly contacting the pressure transducer in furtherance of detecting, monitoring, recording, etc. same.

With initial reference to FIGS. 1 & 2, there is generally and collectively shown elements of an advantageous diagnostic drainage catheter assembly, namely, and broadly, an indwelling urinary drainage (Foley) catheter 10 (FIG. 1) and a vesical pressure measurement system or kit 40 (FIG. 2). As will be subsequently taken up, the system of FIG. 2, or a variant thereof, via a balloon adaptor thereof, is quickly and reliably operably affixable with/to an indwelling urinary drainage catheter previously deployed for selective drainage of urine from the bladder. Advantageously, the catheter balloon adaptor is easily united with the indwelling catheter; a gloved clinician can readily, swiftly and securely attached the adaptor, even with one hand in the case of translational engagement, and no uncertain terms, without resort to hardware or the like. Moreover, it is believed desirable and advantageous to establish or otherwise provide an interface that is tamper proof or at least tamper evident. While a standard 2-way Foley is shown, use of the system/kit is not so limited, with a standard 3-way Foley and alternate indwelling catheters (e.g., Duette by Poiesis Medical, Florida, USA) likewise contemplated and suitable.

System or kit 40 advantageously and desirably includes a urodynamic data system 50 characterized by a pressure sensor 52 for vesical pressure measurement during both bladder filling and emptying states, and a processor/controller 54, programmable or otherwise, for receiving, monitoring, processing, and/or displaying select urodynamic patient parameters comprising sensed/monitored pressure data, and a catheter balloon adaptor 70 for operably uniting the pressure sensor of the urodynamic data system to a balloon inflation valve of the catheter. While the system may take numerous forms, in all its forms it is contemplated to be a portable, totable, etc. system intended for multiple, and even other uses as circumstance may warrant, unlike the catheter balloon adaptor which, like the catheter itself, is a limited use item or device.

Preferably, but optionally, the system or kit further includes an isolation tubing assembly 90 interposed between balloon adaptor 70 and pressure sensor 52 as shown, and/or a fluid flow regulator (not shown) for operative combination with urine conduit 18 of catheter 10 (FIG. 1/1A). Advantageously, but not necessarily, the isolation tubing assembly may be integral to the catheter balloon adaptor (i.e., a built-in feature of the adaptor assembly). The fluid flow regulator may take the form of a Cunningham clamp or a Flip Flo® catheter valve from Bard Medical, Covington, Ga., USA, however, it is believed desirable to provide a selectively actuated valve for operative linkage to/with the urodynamic data system.

Preferably, but optionally, urodynamic data system 50 is or may be characterized by, among other things as will be latter taken up, an output device 56 (e.g., a phone, tablet, PC, etc.) operably linkable to processor 54, a database 58 accessible by processor 54, a weighing scale 60 (see e.g., Applicant's EasyFlo Stand-alone Uroflow system) operably linkable to or adapted for integration with processor/controller 54 for determining a mass of collected fluid discharging from the urine conduit of the Foley catheter in furtherance of determining a fluid flow rate, electromyography (EMG) electrodes 62 operably linkable to processor/controller 54 in furtherance of ascertaining patient abdominal and/or perianal activity, and a clamp or fluid flow regulator (not shown) to permit urine accumulation in the bladder, such device operably unitable with the indwelling urinary drainage catheter to as to impart a resistance to fluid flow from the bladder via the drainage lumen thereof.

In connection to release of accumulating urine from the bladder, there is oftentimes a concern that patients who do not have sensation, or are cognitively impaired, will not open the drain line and empty the bladder, resulting in overfilling of the bladder, and reflux of urine into the kidneys. A selectively actuatable valve may be suitably utilized, the valve selectively actuatable, i.e., opened, based on either a select time interval (e.g., every 4 hours), or based on other conditions, e.g., such as vesical pressure), or a combination of several conditions. Moreover, it is to be noted that the weighing scale may be readily adapted to include an alarm/alarm mode to indicate when the valve is opened and the urine is draining, or if no urine or a low volume of urine empties into a collection device (e.g., a drainage bag). These conditions could be caused by a blockage in the catheter or by a lack of urine production by the patient, both of which are clinical events potentially requiring intervention.

Figure 3:
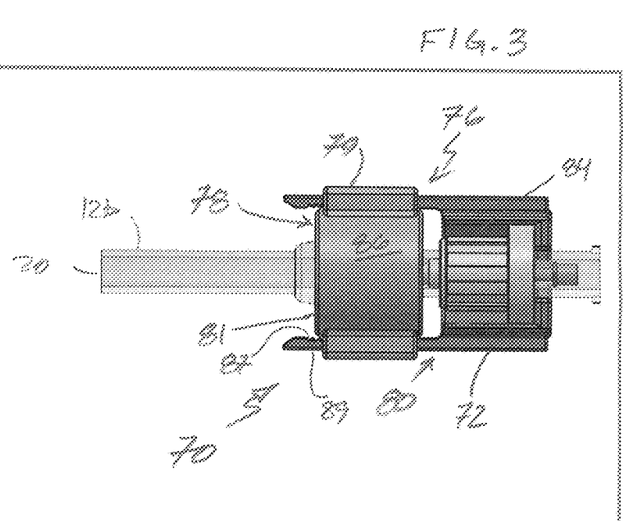
FIG. 3 depicts, side elevation, a contemplated assembly of the system of FIG. 2 for operatively uniting a pressure sensing subassembly to the catheter.
Figure 5:
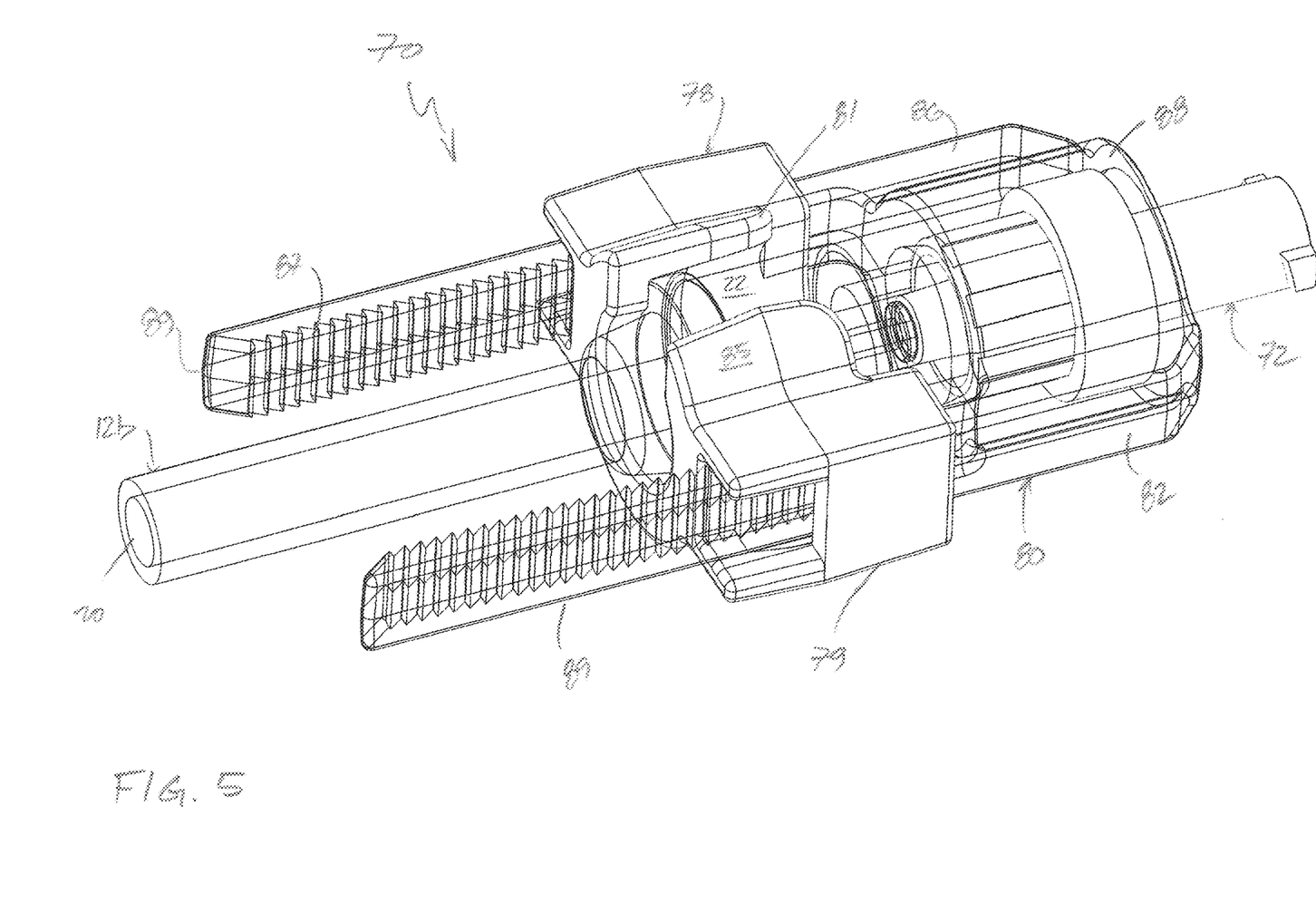
FIG. 5 depicts, perspective overhead view from the left, a further contemplated assembly for operatively uniting a pressure sensing subassembly to the catheter, elements thereof being see-thru to reveal underlying detail, in operative combination with a balloon inflation valve of an indwelling urinary drainage catheter.
Figure 7:
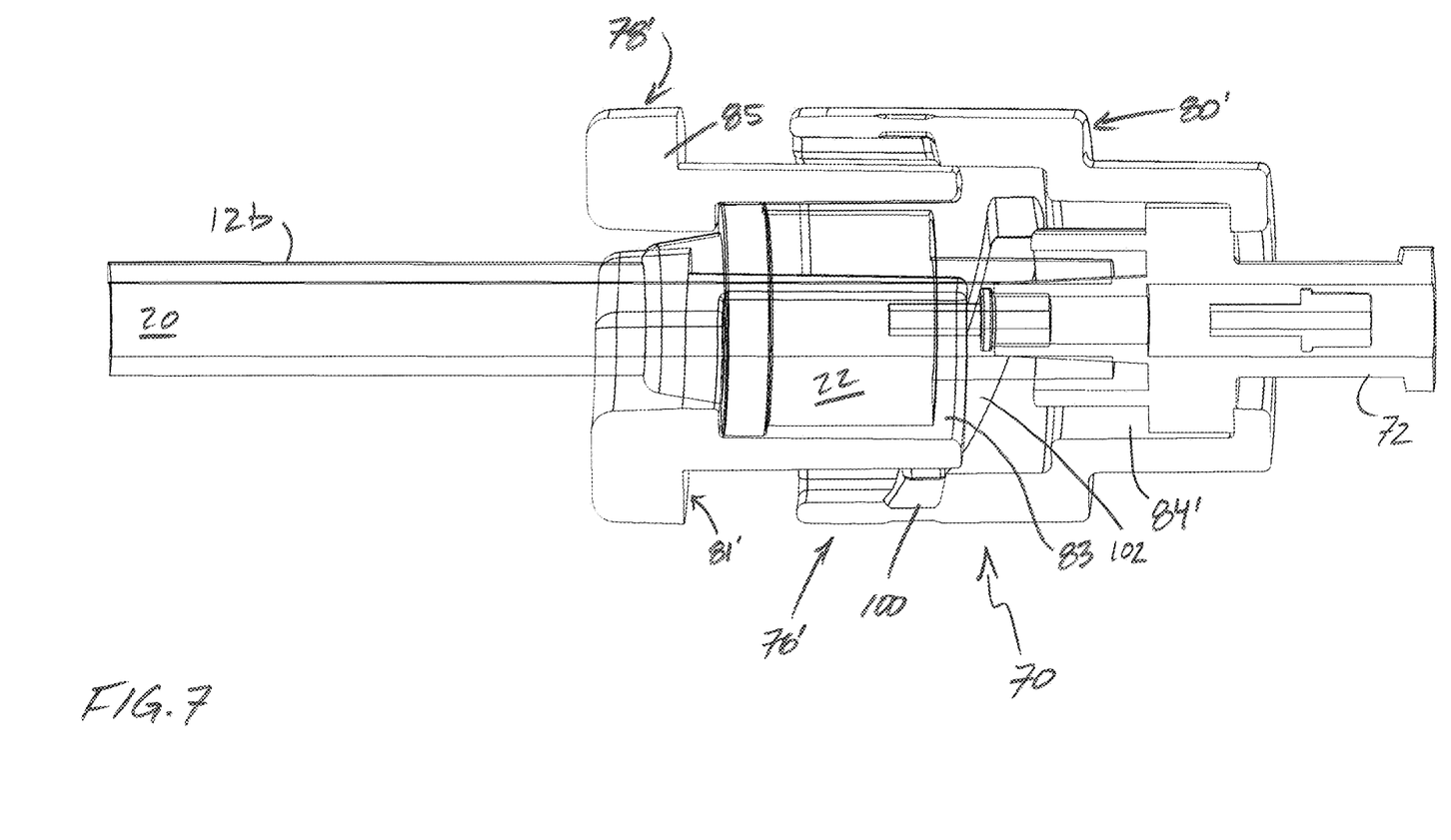
FIG. 7 depicts, axial section view, the combination of FIG. 6.

With particular reference now to the catheter balloon adaptors of each of FIGS. 3 & 5, and with passing reference to the alternate adaptor embodiment of FIG. 7, adaptor or assembly 70 advantageously includes an adaptor valve 72 for operatively linking balloon inflation valve 22 with an apparatus for sensing, measuring, or monitoring select urodynamic parameters (e.g., urodynamic data system 50), and a housing 76. Adaptor housing 76 includes a balloon inflation valve portion 78, and an adaptor valve portion 80, the portions operably uniteable (e.g., selectively affixable) in furtherance of establishing and maintaining a secure interface between balloon inflation valve 22 and adaptor valve 72. More particularly, one housing portion of the housing portions is urgingly advanceable in respect of another housing portion in furtherance of establishing a quick, secure union of the adaptor or adaptor assembly to/with the catheter. As will be later discussed, the housing portions are adapted to be urgingly drawn together, e.g., via translation (FIG. 3 or FIG. 5) or rotation (FIG. 7) of one housing element relative to another.

Adaptor valve 72 of balloon adaptor 70 mates with catheter inflation valve 22, and advantageously comprises a luer activated valve. The adaptor valve is characterized by a stem which deactivates the luer-activated valve of the catheter's balloon fill line. For example, and as shown, a preferable adaptor valve is a female to male luer (Qosina PN QOS5401036SN).

Housing 76 of balloon adaptor 70 is advantageously, but not necessarily a two-part housing as shown. Via after described preferable non-limiting structures, the housing may be assembleable about a valved union between, among and for the catheter and an apparatus for sensing, measuring, or monitoring select urodynamic parameters. Contrariwise, and advantageously, the adaptor assembly is provided in a pre-loaded state (i.e., the housing portions are operatively linked, via a cooperative interface, in a spaced apart condition, the assembly being tensioningly received or manipulated about the catheter inflation valve, with the adaptor valve housing portion translatingly urged into operative engagement therewith subsequent to urgingly advancing the adaptor valve housing portion towards inflation valve housing portion).

Figure 4:
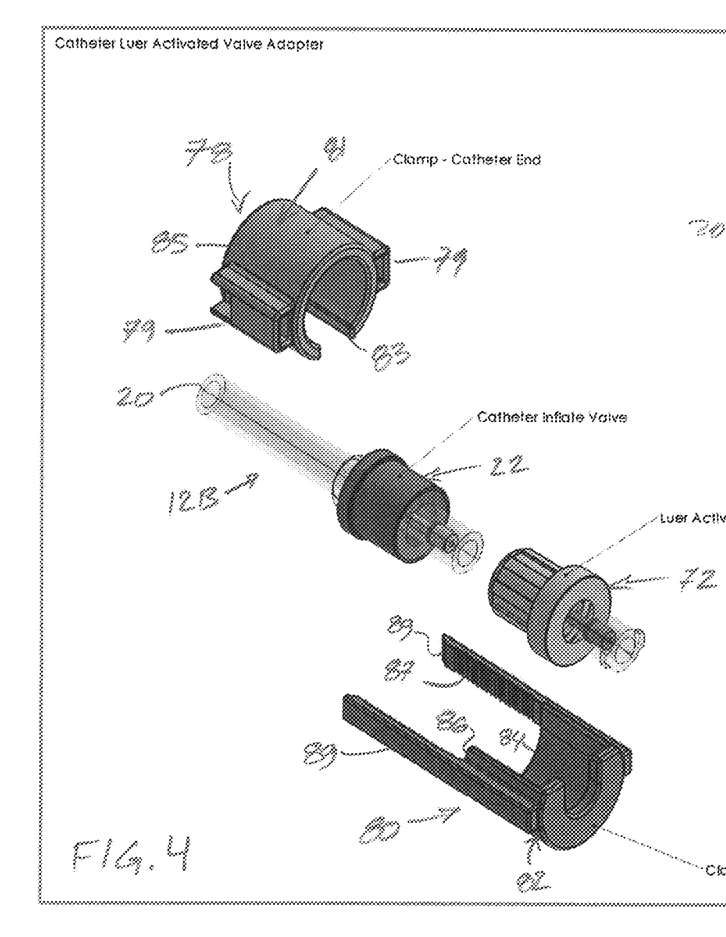
FIG. 4 depicts, exploded perspective view, the assembly of FIG. 3.

Balloon inflation valve portion 78 of housing 76 is configured to circumscribe balloon inflation valve 22. This housing portion (i.e., housing body portion) is generally characterized as a cuff or sleeve comprised of a circumferential or partially circumferential sidewall 81 which at least partially circumscribes the balloon inflation valve. The sidewall includes interior 83 and exterior 85 surfaces (FIG. 4). Notionally, while this housing portion may function as a spring clip in furtherance of ready securement about the balloon inflation valve, it is advantageously received about the inflation segment body of the catheter via a sidewall groove, with the so positioned housing portion slide over the inflation valve.

Interior surface 83 of sidewall or partial sidewall 81 is advantageously adapted (e.g., contoured) to seat or at least cooperatively receive a portion of the balloon inflation valve. Exterior surface 85 of sidewall or partial sidewall 81 is adapted to cooperatively engage, for example and advantageously, urgingly engage with and irreversibly receive adaptor valve portion 72 of housing 70. More particularly, balloon inflation valve housing body portion 78 is advantageously equipped with a guide or retainer for receipt of a portion or portions of the adaptor valve housing body portion 80, for example, opposingly paired guides 79 extend from exterior surface 85 thereof as shown. The guide or retainer advantageously functions to aid in quick reliable housing assembly (i.e., registration of the housing portions) and to secure the housing portions about an operative union of the adaptor valve and balloon inflation valve to thus fortify that interface, namely, a zip or ratcheted interface.

Adaptor valve portion 80 of housing 76 generally circumscribes adaptor valve 72. This housing portion (i.e., housing body portion) is generally characterized as a cuff or sleeve having a circumferential or partially circumferential sidewall 82, which at least partially circumscribes adaptor valve 72, and an end wall 88 through which a portion of adaptor valve 72 is passable. Sidewall 82 includes interior 84 and exterior 86 surfaces (FIG. 4). Advantageously, the adaptor valve housing portion and the adaptor valve are provided in the form of an integrated subassembly (FIG. 5).

Interior surface 84 of sidewall or partial sidewall 82 is advantageously adapted (e.g., contoured) to seat or at least cooperatively receive a portion of adaptor valve 72. Exterior surface 86 of sidewall or partial sidewall 82 is adapted to cooperatively engage, for example and advantageously, urgingly unite with balloon inflation valve portion 78 of housing 76. More particularly, adaptor valve housing body portion 80 is advantageously adapted to include or carry a depending element or elements receivable in the guide or retainer of the balloon inflation valve housing body portion, for example, opposingly paired arms 89 as shown. In furtherance of establishing a secure translating engagement for, between and among the housing portions, either or both of the arms 89 and retainers 79 of their respective housing portions 80, 78 may be suitable adapted to form an interference fit, for example, a portion of mating surfaces of the arms and retainers includes a toothed surface, see e.g., toothed surface 87 of arm 89 of assembly valve housing body portion 80. Again, as was noting in passing, such interface, especially in a preloaded assembly configuration, provides a supremely easy to affix and adjust (snug) the assembly in relation to the catheter balloon valve, and, with the noted structures, establish an interface one that is not readily undone or reversed.

Figure 6:
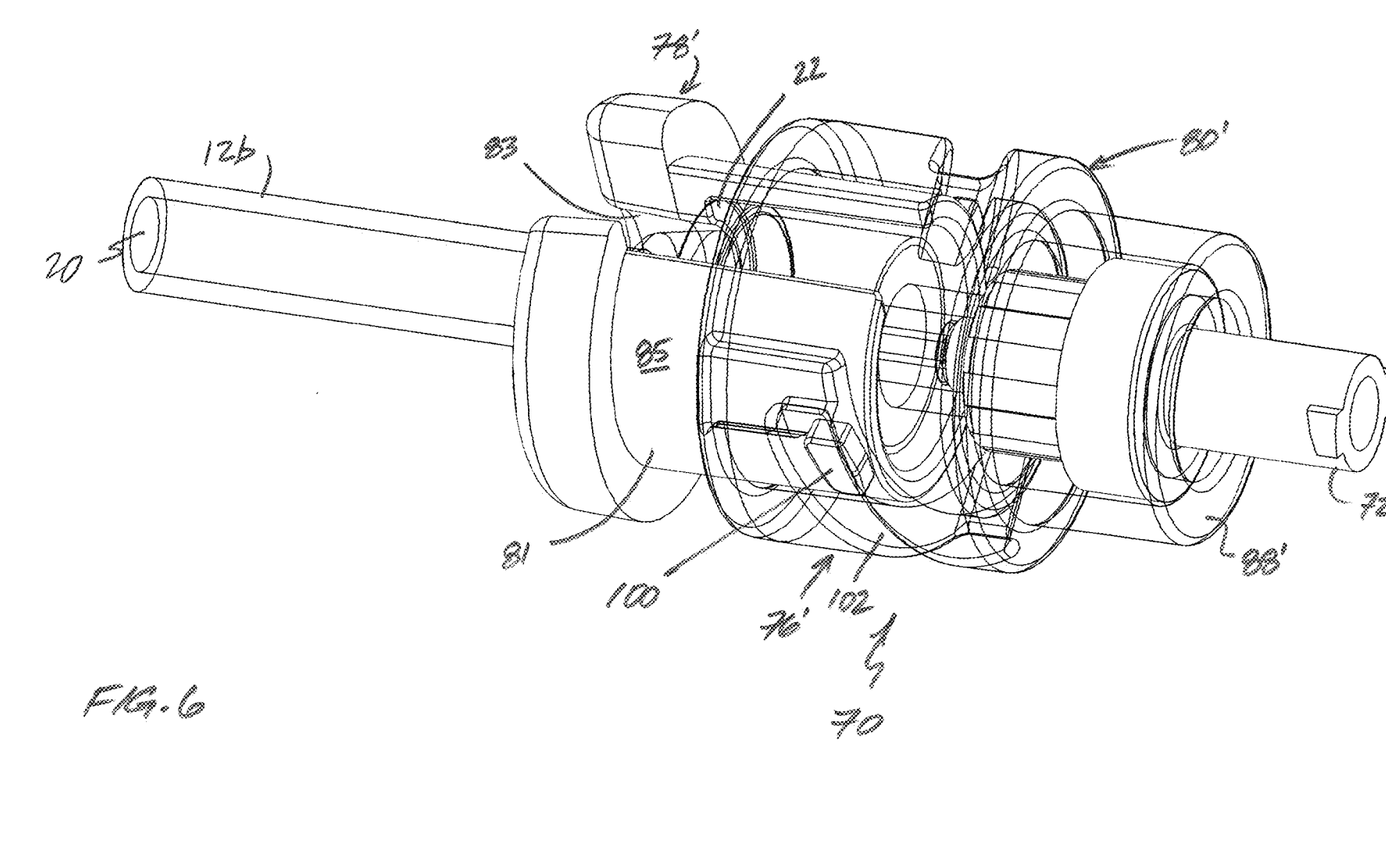
FIG. 6 depicts, perspective overhead view from the right, a further contemplated assembly for operatively uniting a pressure sensing subassembly to the catheter, elements thereof being see-thru to reveal underlying detail, in operative combination with a balloon inflation valve of an indwelling urinary drainage catheter.
Figure 9:
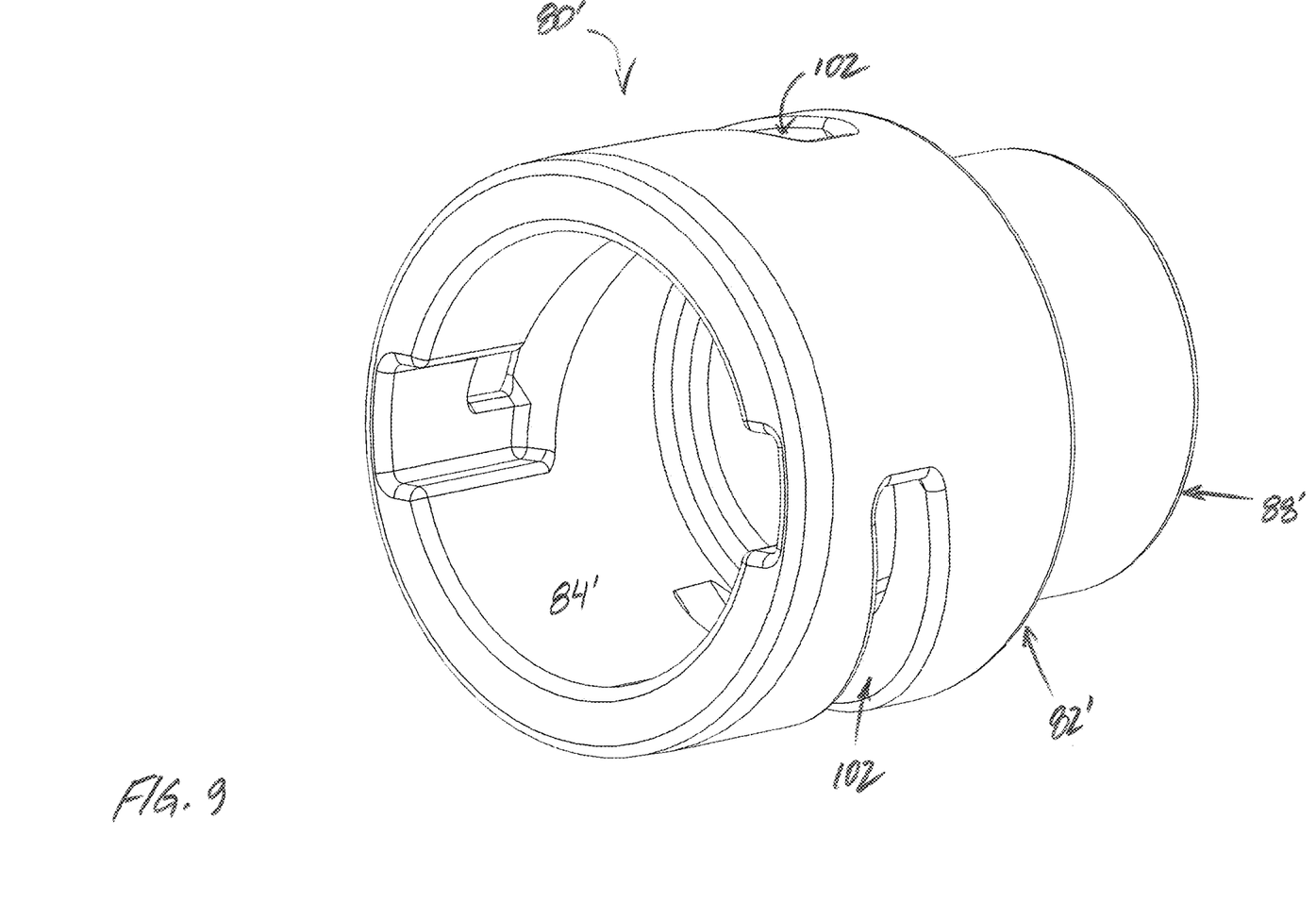
FIG. 9 depicts, perspective overhead view from the left, a second housing portion of a housing of the assembly of the combination of FIG. 6; and, FIG. 10 is a representative depiction of pressure, flow and applied outlet resistance as a function of time during distinct sequential bladder storage anomaly assessment phases, with illustrative tabulated for the depicted parameter versus time relationships supplied.

With reference now to the catheter adaptor assembly of FIG. 6 and the particulars thereof depicted in FIGS. 7-9, adaptor or assembly 70' advantageously includes an adaptor valve 72' for operatively linking balloon inflation valve 22 with an apparatus for sensing, measuring, or monitoring select urodynamic parameters (e.g., urodynamic data system 50 (FIG. 2)), and a housing 76'. Adaptor housing 76' includes a balloon inflation valve portion 78' (FIG. 8), and an adaptor valve portion 80' (FIG. 9), one housing portion of the housing portions being urgingly advanceable in respect of another housing portion in furtherance of establishing and maintaining a secure interface between balloon inflation valve 22 and adaptor valve 72' (i.e., establishing a quick, secure union of the adaptor or adaptor assembly to/with the catheter). As will be subsequently discussed, the housing portions are adapted to be urgingly drawn together via rotation of one housing element relative to another.

As early described, balloon inflation valve portion 78' of housing 76' (FIG. 8) is configured to circumscribe balloon inflation valve 22. This housing portion (i.e., housing body portion) is generally characterized as a cuff or sleeve comprised of a circumferential or partially circumferential sidewall 81' which at least partially circumscribes the balloon inflation valve. The sidewall includes interior 83' and exterior 85' surfaces. Notionally, while this housing portion may function as a spring clip in furtherance of ready securement about the balloon inflation valve, it is advantageously received about the inflation segment body of the catheter via a sidewall groove, with the so positioned housing portion slide over the inflation valve.

Interior surface 83' of sidewall or partial sidewall 81' is advantageously adapted (e.g., contoured) to seat or at least cooperatively receive a portion of the balloon inflation valve. Exterior surface 85' of sidewall or partial sidewall 81' is adapted to cooperatively engage, for example and advantageously, urgingly engage adaptor valve portion 72' of housing 70'. More particularly, balloon inflation valve housing body portion 78 is advantageously equipped with a key 100 (e.g., opposing keys as shown) which is operatively received by a portion of the adaptor valve housing portion. The key advantageously functions to aid in quick reliable housing assembly (i.e., registration of the housing portions) and to secure the housing portions about an operative union of the adaptor valve and balloon inflation valve to thus fortify that interface via a rotational urged engagement for, between and among the housing portions.

Adaptor valve portion 80' of housing 76' generally circumscribes adaptor valve 72. This housing portion (i.e., housing body portion) is generally characterized as a cuff or sleeve having a circumferential sidewall 82', which circumscribes adaptor valve 72, and an end wall 88' through which a portion of adaptor valve 72 is passable. Sidewall 82' includes an interior surface 84' having a portion adapted, for example, via inclusion of a relief area or segment, for initial receipt of key 100 of housing portion 78. Sidewall 82' includes a keyway 102 (e.g., opposing keyways as shown) in the form of a slot or the like having an end that terminates at the relief area of the interior surface of the sidewall. Advantageously, the keyway is off-set from vertical, integration of the key of the inflation valve housing body portion with the keyway of the adaptor valve housing portion via a twisting motion resulting in a rotatingly urged engagement of, for and between the housing portions, and thus, a fortified union between the housed valves.

With renewed reference to the system of FIG. 2, it is believed both advantageous and desirable to isolate the fluid/liquid of the balloon (i.e., balloon environment) from the pressure sensing element (i.e., avoid direct contact/engagement of the sensor/sensed media). Toward that end, the contemplated system further, but not necessarily, includes isolation tubing assembly or extension 90 which operatively links the catheter, via the housing (more particularly, the adaptor valve thereof), to and with the pressure sensing element.

Isolation tubing extension 90 is characterized by a male luer 94 (e.g., a Qosina 71627 luer) on the catheter end of the conduit (i.e., tube 90), more particularly, the luer is carried upon a length (e.g., 4 inch long length) of air-tight tubing (e.g., Qosina T2005 tubing) which in turn is connected to a valved female luer lock connector 96 (e.g., Qosina QOS5401036SN luer lock) for operative receipt of pressure sensor 52. The catheter end valve essentially disables the catheter balloon adaptor valve upon engagement therewith. A contemplated alternative, advantageous approach includes integrating the isolation tubing extension to the housing or a portion thereof, thus rendering the catheter end valve of the extension assembly a surplus.

The benefit of the isolation tubing is that it can be utilized to isolate the liquid in the balloon from the pressure sensing element, allowing the pressure sensing element to be uncontaminated by the liquid. Without the isolation tubing, the sensing element of a pressure transducer comes in direct contact with the liquid in the balloon. The isolation tubing is open at one end, and valved at the other end. It contains an initial volume or fluid charge (e.g. air) which acts as a buffer between the liquid in the balloon and the pressure transducer.

With continued reference to FIG. 2, pressure sensor 52 is advantageously, but not exclusively provided in the form of a chip based sensor, the sensor having an integral luer fitting for ready union with either of a free end of the isolation tubing extension or assembly (FIG. 2), or the adaptor valve. A preferred embodiment of the pressure sensor comprises a single use pressure sensor, polycarbonate, with luer (sterile), PN PRESS-S-000 from PendoTECH, Princeton, N.J., USA.

Processor/controller 54 of urodynamic data system 50 functions advantageously to, for example, at least monitor/monitor-display, and transmit sensed pressure from pressure sensor 52. A preferred embodiment of the processor/controller comprises a PressureMAT™ Sensor Monitor from PendoTECH, the unit further providing a signaling/alarm functionality. Moreover, inclusion of one or more data ports in/for the processor/controller is believed desirable and advantageous, with attendant data acquisition and/or management software likewise desirable. Towards that end, a preferred processor is further characterized by PressureMAT Data Acquisition Software from PendoTECH. As will subsequently presented, processing further contemplates comparison of received urodynamic patient parameter values as a function of time and/or select comparison with a database of urodynamic parameter values in furtherance establishing and/or utilizing a normative database which describes, for instance, the relationship between vesical pressure at different states and voiding symptoms.

While there are potential disadvantages of measuring pressure through a balloon line, e.g., adaptation of the balloon inflation valve for union to a pressure sensor arguably increases the incidence of inadvertent balloon leakage, and measurements premised upon a less than optimally positioned anchor balloon, there are greater advantages to such approach. For instance, the balloon chamber (i.e., volume delimited by the balloon) is completely isolated from the bladder, therefore there is no risk that the pressure measurement will result in contaminants traveling through the lumen of the line to/into the bladder of a patient. Moreover, the balloon line can be filled with a fixed column of fluid (i.e., liquid or gas (e.g., water or air)), resulting in improved measurement accuracy by the pressure transducer or the like. Further still, the measurement of vesical pressure can be made without concern for the amount of urine in the bladder, and the measurement of pressure does not implicate use of the urine drainage line, thusly, that functionality of/for the indwelling urinary drainage catheter is preserved.

The contemplated bladder vesical pressure determination can be implemented with either of a single balloon or two balloon urinary drainage catheter. Moreover, implementation is contemplated with either of indwelling urinary drainage catheters (i.e. Foley style), or intermittent urinary drainage catheters.

In the single balloon embodiment, the balloon is filled through a valve that allows the connection to a pressure transducer. A pressure transducer can be utilized that allows for a fixed column (i.e., volume) of fluid (i.e., liquid or gas) to be introduced into the line. Alternatively, a traditional syringe can be used to fill the balloon line. Once the balloon is filled, vesical pressure can be monitored continuously or selectively, without concern about the amount of urine in the bladder and without affecting the urine drainage properties/functionality of the catheter.

In the two balloon embodiment, vesical pressure can be measured in a secondary balloon that is not the bladder retaining anchor (i.e., the distal balloon). The primary retaining balloon can be traditionally filled (i.e., using a one-way valve) and placed (i.e., at the bladder neck). A second balloon, which may simply act as a vesical pressure sensor or also act, for example, to prevent the bladder wall apex from resting on the top of the catheter, would be filled with a column of liquid or gas (i.e., volume of fluid) and vesical pressure continuously, intermittently and/or selectively monitored.

There are two main advantages to a two balloon embodiment: (a) the measurement of vesical pressure does not change the design of the one-way valve of the retaining balloon, mitigating any additional risk of retaining balloon deflation; and, (b) the placement of the balloon indicating vesical pressure can be placed in an optimal location to more accurately reflect vesical pressure. For example, if the second balloon is placed above the retaining balloon, it can be assured of not being in contact with the bladder neck. It should be noted that these two advantages may also be realized with an intermittent catheter with a single balloon design that does not utilizing a retaining balloon. The single balloon could be placed optimally, similar to the placement methodology with traditional urodynamic measurement catheters.

In advance of particulars relating to or for select contemplated operational sequences, diagnostic methods and/or clinical protocols preferably, but not exclusively, enabled by aforementioned systems/assemblies (e.g., real time sensing/monitoring of vesical pressure during catheter indwell), and assessment particulars, some initial comments are warranted.

Catheter management leveraging vesical pressure measurement via an indwelling urinary drainage catheter is compelling. Real time monitoring of vesical pressure, urine discharge rates, abdominal EMG and patient bladder sensation are representative, readily ascertainable parameters aiding assessment of bladder storage anomalies. Moreover, contemplated approaches herein after taken up have utility for baseline measurement in relation to surgery candidates (i.e., pre-surgical benchmarking).

Indwelling urinary catheter removal is predicated upon establishment of a vesical pressure adequate for the given patient to void (i.e., self-void vesical pressure). A key element of the assessment is to determine how much the detrusor muscle, a/k/a detrusor urinae muscle contracts during the voiding phase, with select targeted exercising, stimulation, and/or conditioning of the detrusor muscle advantageously improving vesical pressure.

The detrusor muscle is a smooth muscle found in the wall of the bladder. It remains in a relaxed passive state or condition to allow the bladder to store urine, and contracts during urination to release urine. Related physiological structures effecting micturition are the urethral sphincter muscles which envelop the urethra to control the flow of urine upon contraction. During urination the detrusor muscle is contracted via parasympathetic branches from the pelvic splanchnic nerves to empty the bladder. At other times the muscle is kept relaxed via sympathetic branches from the inferior hypogastric plexus to allow the bladder to fill.

Beyond the threshold operation of sensing and measuring vesical pressure during catheter indwell using a balloon fill line thereof, several advantageous, non-limiting operations or operational sequences are illustratively noted. The following representative bladder storage anomaly assessment actions are advantageously, but not necessarily facilitated via utilization of the heretofore disclosed assemblies/devices, and while desirably relying upon an indwelling urinary drainage catheter, they need not be so limited.

For example, a first operational sequence contemplates obtaining a baseline value of vesical pressure at the time of catheter deployment and upon confirmation that the patient is in retention. Continuous or periodic measurements of vesical pressure via the previously placed catheter are thereafter obtained, with a formulaic identification/prediction (e.g., via an improvement in vesical pressure pattern identification) that the catheter can be removed, achieved, with successful voiding by the patient likely resulting.

In a further second contemplated operational sequence, vesical pressure at different states is compared/comparable to a normative database which describes the relationship between vesical pressure at different states and voiding symptoms.

In a further third contemplated operational sequence, vesical pressure data informs a determination that a patient has vesical pressure adequate to successfully void absent a bladder outlet obstruction. If a patient could not adequately void after catheter removal, bladder outlet obstruction could be diagnosed and in a male patient, a temporary prostate stent (e.g., The Spanner® from SRS Medical Systems, LLC, MA, USA) could be implanted. The measurement of vesical pressure could predict whether a patient could successfully void with a temporary prostate stent.

In a further fourth contemplated operational sequence, a pinch valve or clamp is applied to the indwelling urinary catheter to allow the bladder to naturally fill without draining through the catheter urine ports. In this manner, vesical pressure can be measured while the patient's bladder is naturally filling. When the clamp is removed and the patient voids, vesical pressure can be measured during the void. These data can be formulaically analyzed to predict if the catheter can be removed and will likely result in successful voiding by the patient.

In a further fifth contemplated operational sequence, measurements of vesical pressure are made and formulaically analyzed to estimate detrusor pressure. Detrusor pressure is defined as the abdominal pressure minus the vesical pressure (i.e., abdominal pressure is characterized by a combination of detrusor pressure and vesical pressure). By monitoring the vesical pressure over time while the patient is at rest and/or when the patient is asked to perform physical activities, e.g., a Valsalva Maneuver, predictive models are enabled in furtherance of predicting the contribution of detrusor pressure to the measured vesical pressure at different times.

In a further sixth contemplated operational sequence, simultaneous measures of abdominal activity using surface EMG electrodes placed on the abdomen are sought. Data from the electrodes provide insight into abdominal pressure, and thus further improve the prediction of detrusor pressure contribution to the measured vesical pressure.

In a further seventh contemplated operational sequence, simultaneous measures of perianal activity using surface EMG electrodes placed on the perineum are sought. Data from the electrodes provide insight into sphincter-detrusor dyssynergia and may be utilized to further predict whether the patient will be able to void without the catheter.

In a further eighth contemplated operational sequence, a granular predictive model for determining indwelling urinary catheter removal is realized. For instance, rather than predicting that the catheter should or should not be removed, an advantageous embodiment of the contemplated system could predict the likelihood, e.g., on a percentage basis, that the patient will be able to void successfully. For example, an analysis of the available data (e.g., combination of collected and reference data) might permit predictive determination that the patient is 82% likely to be able to successful void. Alternatively, an analysis of the available data might permit a further predictive determination as to the likelihood that the patient could void to a pre-specified, post-void residual, or the likelihood that the patient would go into acute urinary retention.

In a further ninth contemplated operational sequence, the predictive model might be supplemented with data beyond the vesical pressure measurements and the EMG measurements. For instance, patient demographics (e.g., age, gender), patient health history, and patient current symptoms data could be incorporated into the predictive model.

In a further tenth contemplated operational sequence, important bladder conditioning or exercising may be effectuated via utilization of an automated safety drainage clamp/valve system. A patient can self-actuate to void in a by-pass mode, and/or a clinician can select automated drainage to prevent an overfill condition, with, via an override, select automated relief drainage possible, and an automated determination of catheter removal via targeted vesical pressure monitoring, including establishment of a predictive removal model and/or patient specific parameter targets achievable.

In addition to the aforementioned illustrative operational approaches, a desirable, advantageous, robust and non-limiting clinical protocol, in relation to an indwelling catheter patient passing urine from their bladder (continuously) to a collection receptacle, is provided, and contemplates:

1. Uniting a urodynamic assessment assembly/kit to the balloon inflation port of an indwelling urinary (e.g., Foley) catheter in furtherance of operatively equipping the balloon line with a pressure sensing element such as a pressure transducer.
2. Optionally utilizing an isolation tubing device to isolate balloon fluid from the pressure sensing element (i.e., indirect versus direct contact; buffering).
3. Operatively linking the pressure transducer to a data recording/processing unit or the like of the urodynamic assessment assembly and to the balloon line.
4. Optionally placing a urine collection receptacle on a weighing scale.
5. Using the recording/processing unit to "zero" a vesical pressure channel thereof and an optional urine mass/volume channel thereof so as to establish a baseline vesical pressure and empty urine drainage receptacle mass respectively.
6. Ceasing urine egress from the bladder via a urine drain line of the indwelling urinary catheter via actuation of a clamp or valve operatively linked thereto.
7. Introducing fluid into the bladder via the urine drain line so as to selectively accumulate introduced fluid in the bladder, advantageously, but not necessarily via gravity feed of the fluid.
8. Selectively measuring (e.g., continuous, semi continuous or periodic) vesical pressure as the bladder is filling.
9. Optionally recording initial volume of the fluid for introduction, and thereafter recording the volume thereof in conjunction with the select vesical pressure measurement during bladder filling.
10. Optionally displaying vesical pressure data, stored or otherwise, via a display/output device of or associated with the data recording/processing unit in real-time.
11. Optionally placing an EMG electrode on the indwelling catheter patient's abdomen to measure abdominal muscle activity, e.g., continuous monitoring during bladder filling and emptying, acquired data used in quantify the abdominal pressure impact on vesical pressure and to ascertain detrusor pressure.
12. Optionally logging of the patient's bladder filling sensation metrics as the patient's bladder is filling, e.g., "first sensation of bladder filling" and "first desire void," with these events marked simultaneous to other collected data (i.e., correlated to/with).
13. Opening a urine drain line when the patient's bladder is full and s/he has a strong desire to void, e.g., clamp removal or valve opening, so as to allow urine in the bladder to drain into the drainage bag, vesical pressure, abdominal EMG activity, urine flow rate and total voided volume thusly ascertained.
14. Analyzing data to determine the status of the patient's bladder function and to determine whether the catheter should be removed, such analysis advantageously automated part-and-parcel of a series of targeted parameters during bladder cycling so as to determine optimal care pathways.

While illustrative method steps have been disclosed, it is believed that enhanced diagnostic information may be suitably obtained via variation of one or more of the contemplated action steps. More particularly, focal areas include, but are not limited to bladder infusion and applied outlet resistance, more particularly still, and as will be subsequently taken up, bladder infusion rate determination and applied outlet resistance variation.

As to the former, clinical protocols generally involve a gravity feed of fluid (e.g. water) into the bladder via the drain port of the indwelling urinary catheter. The start time of the infusion and the end time of the infusion are recorded, with a visual determination the amount of water infused made. For example, with reference to FIG. 10, a total fluid volume of 350 ml over 300 seconds was infused. While no direct measurement of the infusion rate during the infusion period was made, in this scenario, there was an average infusion rate of 1.167 ml/s over the infusion period.

In the context of the of the contemplated bladder filling/emptying assessment, the bladder is increasing in fluid pressure during the infusion process or procedure. Infusion rate modeling may be readily conducted in light of securing values for a variety of variables as a function of time, e.g., and without limitation, total infused fluid volume, total infusion time, and measured vesical pressure at select points in time so as to yield an infused volume rate throughout the bladder filing phase. Via measurement of the change in pressure differential at the ends of the infusion fluid passage, in combination with the average rate of infusion, infusion rates at each select point during the infusion may be ascertained, and infused volume estimated.

As to the latter, enhanced diagnostic information may be suitably obtained by customizing the manner in which the urine drain line is clamped and released. Traditionally, the line is either closed, during bladder filling, or opened, during bladder emptying; a binary fluid flow condition—on or off.

A contemplated advantageous alternate approach has the bladder emptying event characterized not only by sensing vesical pressure via a pressure sensor during a bladder emptying event, but also by an application of variable resistance to fluid flow from the bladder. The application of variable resistance to fluid flow from the bladder advantageously results in a pulsed fluid flow, either regular or irregular. Moreover, the application of variable resistance to fluid flow from the bladder may take the form of first and second applied resistances, the first applied resistance corresponding to a no flow condition from the indwelling urinary catheter, the second applied resistance corresponding to a maximum flow condition from the indwelling urinary catheter, the applied variable resistance characterized by alternating between the applied resistances.

Mechanical means (i.e., a flow regulator, e.g., a valve) may be suitable selected and utilized to prohibit fluid passage during bladder filling, and during bladder emptying, via actuation of the mechanical means, to vary the effective discharge resistance so as to simulate the effect of urethral resistance, such as that found in patients with Benign Prostate Hyperplasia (BHP). By adjusting the outlet resistance, the vesical pressure-outlet resistance-urine flow rate relationships are readily established to further determine the optimal care pathway.

Figure 10:
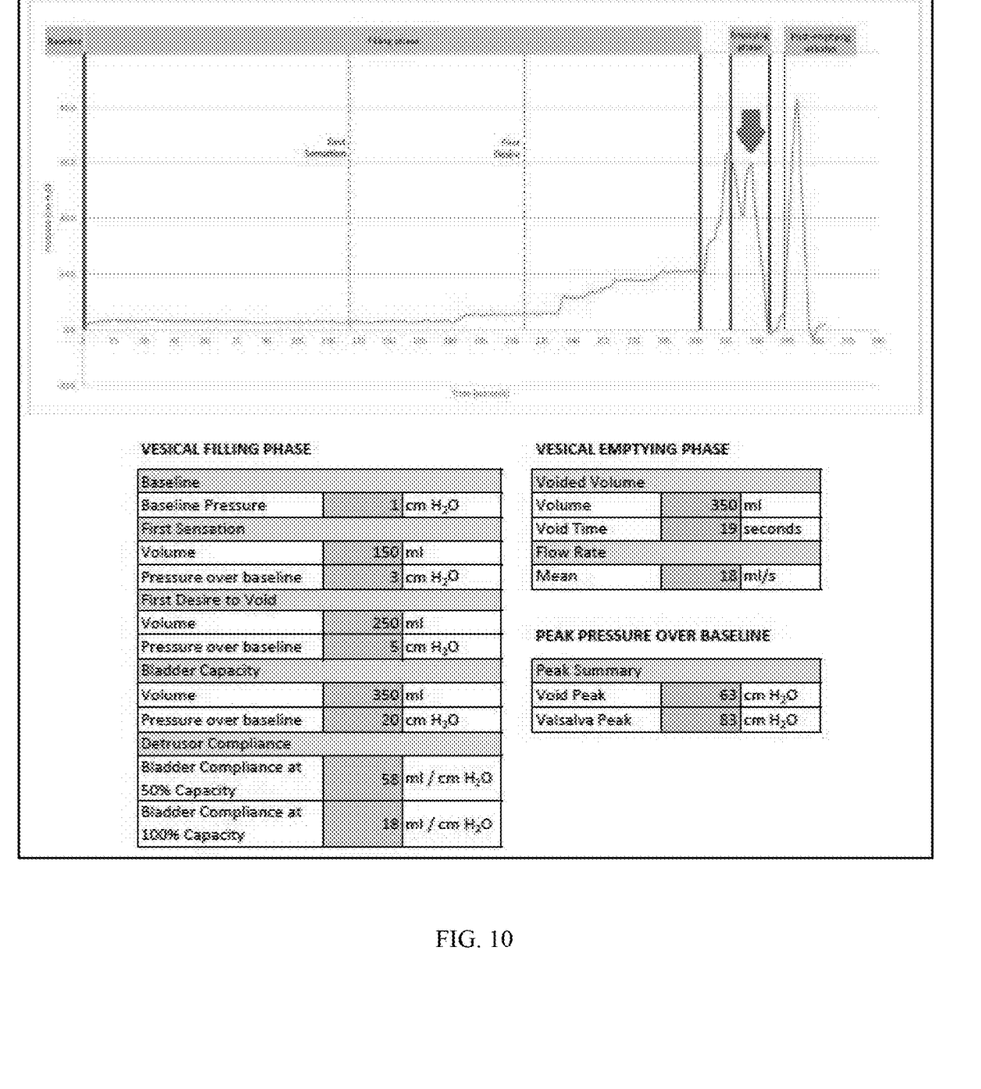

Moreover, and significantly, pulsing the fluid discharge flow via actuation or manipulation of the valve between open and closed states, conditions or configurations, during the void, can result in the stimulation of a bladder contraction. This phenomenon is illustrated in the graphic of FIG. 10 where an arrow indicates a bladder contraction that occurs during the void as a result of a large imparted increase in the outlet resistance.

By adjusting the outlet resistance, the vesical pressure-outlet resistance-urine flow rate relationships can be established to further determine an advantageous, right fit care pathway, specifically, changes to the outlet resistance during the void, including pulsed changes can be advantageously utilized. A regular pulsed change from "open" to "closed" can result in a measurable bladder response which may be a "litmus test" for catheter removal.

What has been described and depicted herein are preferred, non-limiting embodiments of Applicant's subject matter, along with some application contexts. Since the elements of the system and/or structures of the assemblies, subassemblies, and/or mechanisms disclosed herein may be embodied in other specific forms without departing from the spirit or general characteristics thereof, some of which forms have been indicated, the embodiments described and depicted herein/with are to be considered in all respects illustrative and not restrictive. Moreover, while nominal operational steps or sequences and/or a protocol have been set forth, and to some degree alternate work pieces and systems, assemblies, etc. with regard thereto referenced, contemplated sequences/protocols are not so limited. Accordingly, the scope of the subject invention is as defined in the language of the appended claims, and includes not insubstantial equivalents thereto.

That which is claimed:

1. A method of assessing bladder storage anomalies via utilization of an indwelling urinary drainage catheter, the method comprising:
    a. providing a urodynamic assessment assembly characterized by a pressure sensor for vesical pressure measurement during either of bladder filling or emptying events, a processor for receiving, processing and/or displaying select urodynamic patient parameters comprising monitored pressure data, and a catheter balloon adaptor for operably uniting said pressure sensor of said urodynamic assessment assembly to a balloon inflation valve of the indwelling urinary drainage catheter, said catheter balloon adaptor directly coupled to the balloon inflation valve;
    b. operably linking said indwelling urinary drainage catheter with said urodynamic assessment assembly;
    c. sensing vesical pressure via said vesical pressure sensor during a bladder emptying event, the bladder emptying event characterized by an application of variable resistance to fluid flow from the bladder via said indwelling urinary drainage catheter; and, d. establishing vesical pressure and/or outlet resistance or flow rate relationships based upon sensed vesical pressure values.

2. The method of claim 1 wherein said application of variable resistance to fluid flow from the bladder via said indwelling urinary drainage catheter results in a pulsed fluid flow from said indwelling urinary drainage catheter.

3. The method of claim 1 wherein said application of variable resistance to fluid flow from the bladder via said indwelling urinary drainage catheter results in a regularly pulsed fluid flow from said indwelling urinary drainage catheter.

4. The method of claim 1 wherein said application of variable resistance to fluid flow from the bladder via said indwelling urinary drainage catheter results in an irregularly pulsed fluid flow from said indwelling urinary drainage catheter.

5. The method of claim 1 wherein a first applied resistance of applied variable resistance corresponds to a no fluid flow condition from said indwelling urinary drainage catheter, and a second applied resistance of applied variable resistance corresponds to a maximum flow condition from said indwelling urinary drainage catheter, said applied variable resistance characterized by alternating between said first applied resistance and said second applied resistance.

6. The method of claim 1 further comprising determining a fluid flow rate for fluid flowing from the bladder via said indwelling urinary drainage catheter during the bladder emptying event.

7. The method of claim 1 further comprising determining a mass of fluid flowing from the bladder via said indwelling urinary drainage catheter during the bladder emptying event as a function of time.

8. The method of claim 1 further comprising sensing vesical pressure via said vesical pressure sensor during a bladder fill event characterized by a no drainage condition for said indwelling urinary drainage catheter.

9. The method of claim 8 wherein said bladder fill event comprises a gravity fluid feed, the method further comprising determining gravity fluid feed rates associated with said gravity fluid feed corresponding to select sensed vesical pressures while fluid fills and accumulates in the bladder.

10. A method of assessing bladder storage anomalies via utilization of an indwelling urinary drainage catheter, the method comprising:

a. providing a urodynamic data system characterized by a pressure sensor for vesical pressure measurement during either of bladder filling or emptying events, and a processor for receiving, processing and/or displaying select urodynamic patient parameters comprising monitored pressure data;

b. providing a catheter balloon adaptor for operably uniting said pressure sensor of said urodynamic data system to a balloon inflation valve of the indwelling urinary catheter, said catheter balloon adaptor directly coupled to the balloon inflation valve;

c. operably linking the indwelling urinary drainage catheter with said urodynamic data system via said catheter balloon adaptor;

d. sensing vesical pressure via said vesical pressure sensor during a bladder fill event characterized by a no drainage condition for said indwelling urinary drainage catheter;

e. sensing vesical pressure via said vesical pressure sensor during a bladder emptying event, the bladder emptying event characterized by an application of variable resistance to fluid flow from the bladder via said indwelling urinary drainage catheter.

\* \* \* \* \*